United States Patent [19]
Johnson

[11] Patent Number: 5,360,391
[45] Date of Patent: Nov. 1, 1994

[54] SHOULDER BRACE

[76] Inventor: Lanny L. Johnson, 4528 Hagadorn, East Lansing, Mich. 48823

[21] Appl. No.: 51,833

[22] Filed: Apr. 26, 1993

[51] Int. Cl.$^5$ .............................................. A61F 13/00
[52] U.S. Cl. ......................................... 602/5; 602/20; 2/45
[58] Field of Search ........................... 602/4, 5, 19, 20; 128/95.1, 99.1, 869, 874, 878, 25 R, 26; 2/44, 45; 482/112, 113, 123, 124

[56] References Cited

U.S. PATENT DOCUMENTS 5,181,906  1/1993  Bauerfeind ............................ 2/45 X Primary Examiner—Richard J. Apley
Assistant Examiner—Beverly A. Meindl
Attorney, Agent, or Firm—Cushman, Darby & Cushman

[57] ABSTRACT

A shoulder brace is provided with two support members each attached at one of its ends to a belt of adjustable length worn about the torso of the user. The support members extend diagonally upwardly across opposite sides of the body whereby their opposite ends are positioned outwardly and above the user's torso. The support members pass through a sleeve adapted to rest on the shoulder of an arm to be supported by the brace. The respective opposite ends of the support members are joined to a support bar from which an arm-receiving sleeve is suspended. By adjustment of the lengths of the support members and by selective bending of said members, the shoulder brace is adapted to fit different body sizes and to suspend the user's arm in a desired position.

24 Claims, 4 Drawing Sheets

SHOULDER BRACE

BACKGROUND OF THE INVENTION

1. Field of the Invention

The invention relates to an arm support device, and in particular, to a shoulder brace for holding the arm away from the side of the body.

2. Description of the Prior Art

A number of braces have been developed to position the shoulder in a particular orientation and/or to hold the arm away from the body. Such braces commonly are used to support a fractured or otherwise injured arm in a proper healing position relative to the body. Necessarily, they often are worn for long periods of time to allow for adequate healing. For example, a shoulder brace may be required for as long as a number of weeks.

Conventional shoulder braces have a number of disadvantages. They typically are heavy, uncomfortable and must be made in many sizes to provide an adequate fit for different sized people. Conventional braces also have several points of attachment to the body and cover a substantial portion of the torso with straps and other securing devices, thus limiting the user's freedom of movement.

SUMMARY OF THE INVENTION

It is an object of the present invention to provide an improved shoulder brace that is of light weight and comfortable to wear. Additionally, it is an object to provide a brace that is easily adjustable and can fit a wide range of body sizes. A still further object of the invention is to provide a brace that has limited contact with the body, thus allowing the user freedom of movement and permitting air circulation over the user's skin.

In accordance with the present invention, the shoulder brace suspends the arm in cantilevered fashion from above, rather than supporting it from below. The brace has two support members each attached at one of its ends to a belt worn about the torso of the user. The members extend diagonally upwardly across opposite sides of the body in the direction of the arm to be supported. The members pass through a sleeve which rests on the shoulder of the arm to be supported. The free ends of the support members, located outwardly of the user's torso, are attached to a rod of adjustable length from which the user's arm is suspended.

Advantages of the present invention are that the brace is lightweight and easily adjustable to most body sizes. Also, substantially all of the user's torso is exposed to air circulation. Thus, the brace is effective in the treatment of body burns where the arm must be supported so as to minimize contact with the patient's chest and side. The highly adjustable nature of the invention also makes the device effective in the treatment of upper extremity fractures or neurovascular injury about the shoulder. The brace additionally lends itself useful in recovery from reconstructive shoulder and elbow surgery.

Other objects, features, and characteristics of the present invention, as well as the methods of operation and functions of the related elements of structure, and the combination of parts and economics of manufacture, will become more apparent upon consideration of the following detailed description of the invention, the appended claims and the accompanying drawings, all of which form a part of this specification, wherein like reference numerals designate corresponding parts in the various figures of the drawings.

DETAILED DESCRIPTION OF THE INVENTION

The improvements achieved the by present invention can be appreciated by first considering the shortcomings of typical prior art shoulder braces.

Figure 1:
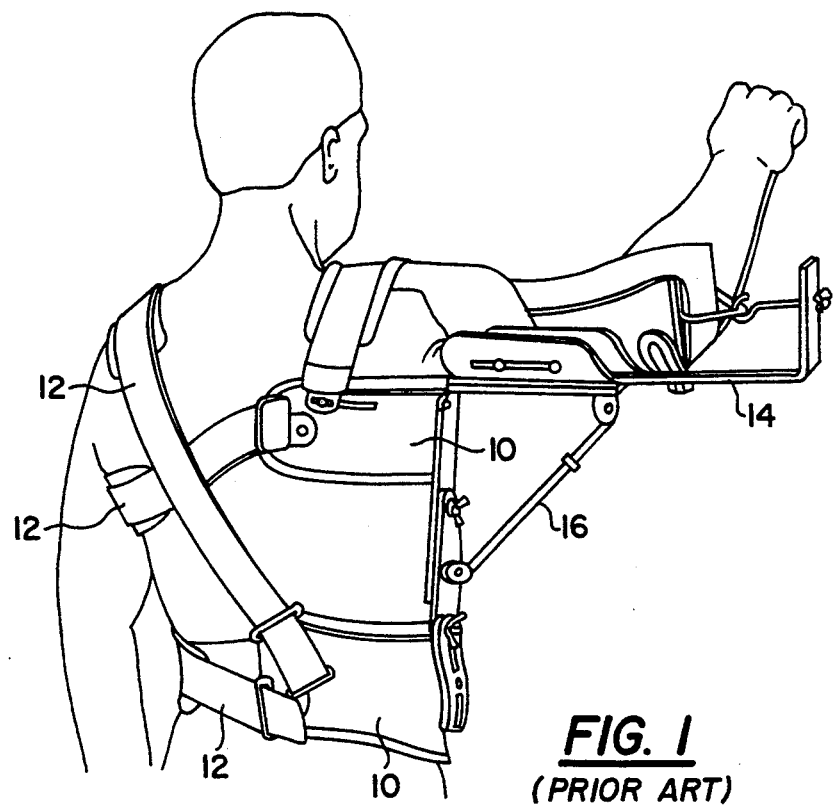
FIG. 1 is a rear perspective view of a conventional shoulder brace.
Figure 2:
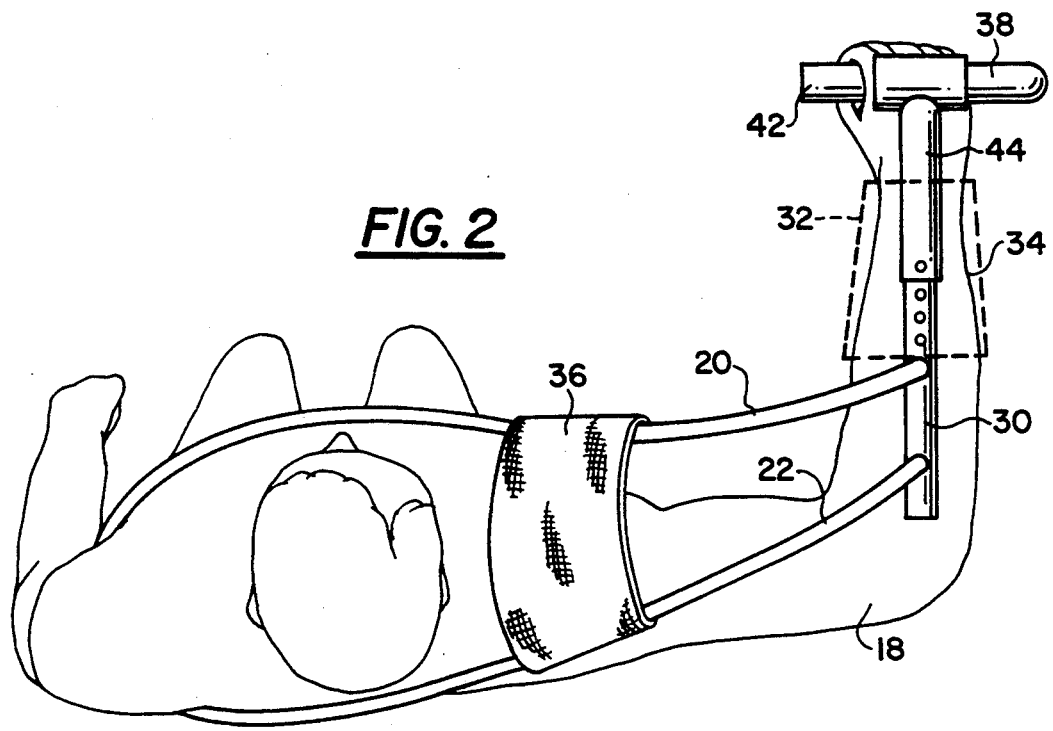
FIG. 2 is a top plan view of the present invention in use.

A convention shoulder brace, shown in FIG. 1, is generally referred to as an "aeroplane splint". It has an attachment portion 10 which is strapped about the trunk of an individual. The attachment portion comprises one or more members having a shape approximating that of the body and extending from the axilla (arm pit) to the hip. These members extend from substantially the front center of the body, around one side, under the arm, to the center of the back. The attachment portion is secured to the body by a number of adjustable straps 12 which extend around the torso and over the shoulders. A rigid arm support member 14 is pivotally connected to the upper attachment portion 10. Member 14 extends from a position proximate the arm pit away from the body to support an arm strapped to the top of the member. Thus, the arm rests upon the support member 14. A strut 16 of adjustable length extends between the arm support member 14 and the attachment portion 10 to correctly position member 14.

The shoulder brace according to the present invention is illustrated in FIGS. 2–5. The brace supports arm 18 of the user by suspending the arm from at least two support members 20, 22. Members 20 and 22 are attached at respective ends 21, 23 to a belt in a manner to be detailed hereinafter. The belt preferably comprises an adjustable counter balance strap 24, the ends of which are connected to a support strap 26 to which the ends 21 and 23 of the support members are connected.

The belt formed by straps 24 and 26 fits about a person's torso. The straps are made of leather, nylon or other suitable material and as required, they may include appropriate padding to accommodate forces to the body applied at different portions of the belt. The respective ends 21 and 23 of support members 20, 22 are removably or fixedly connected adjacent opposite ends of the support strap 26 by attachment means common in the art. For example, they may be received in pockets (not shown) provided on the outer surface of the support strap 26.

From strap 26, the support members 20, 22 extend diagonally upwardly across opposite sides of the body towards the shoulder of the arm to be supported. The support members are curved to conform to the body's contour. The members may be made of metal tubing, such as aluminum. Alternatively, they can be plastic, such as resin impregnated with strengthening fibers, e.g., fiberglass. Metal support members are preferred because they are bendable to allow for more accurate fitting of the brace to conform to a person's torso.

Figure 3:
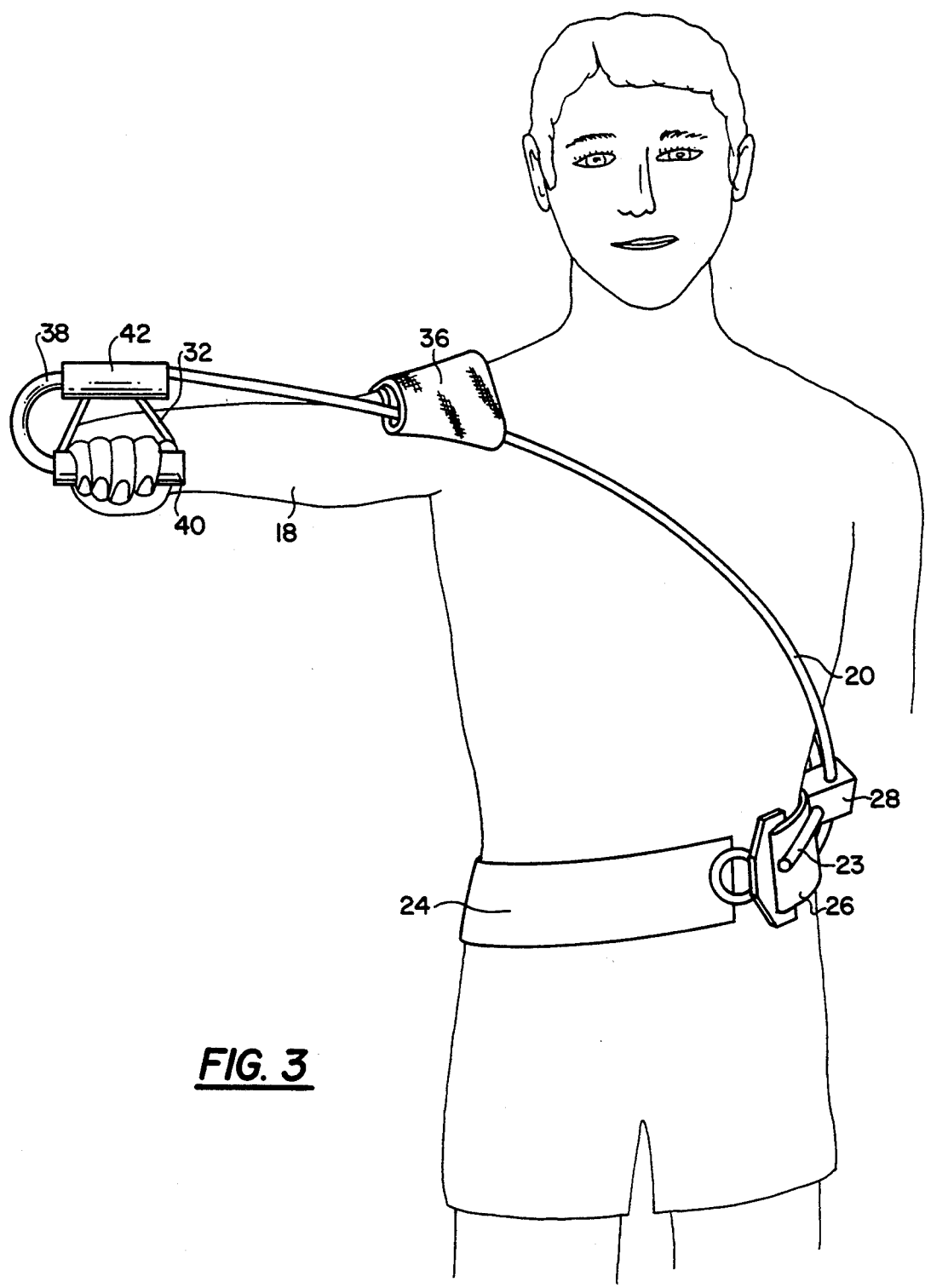
FIG. 3 is a front elevational view of the invention shown in FIG. 2.
Figure 4:
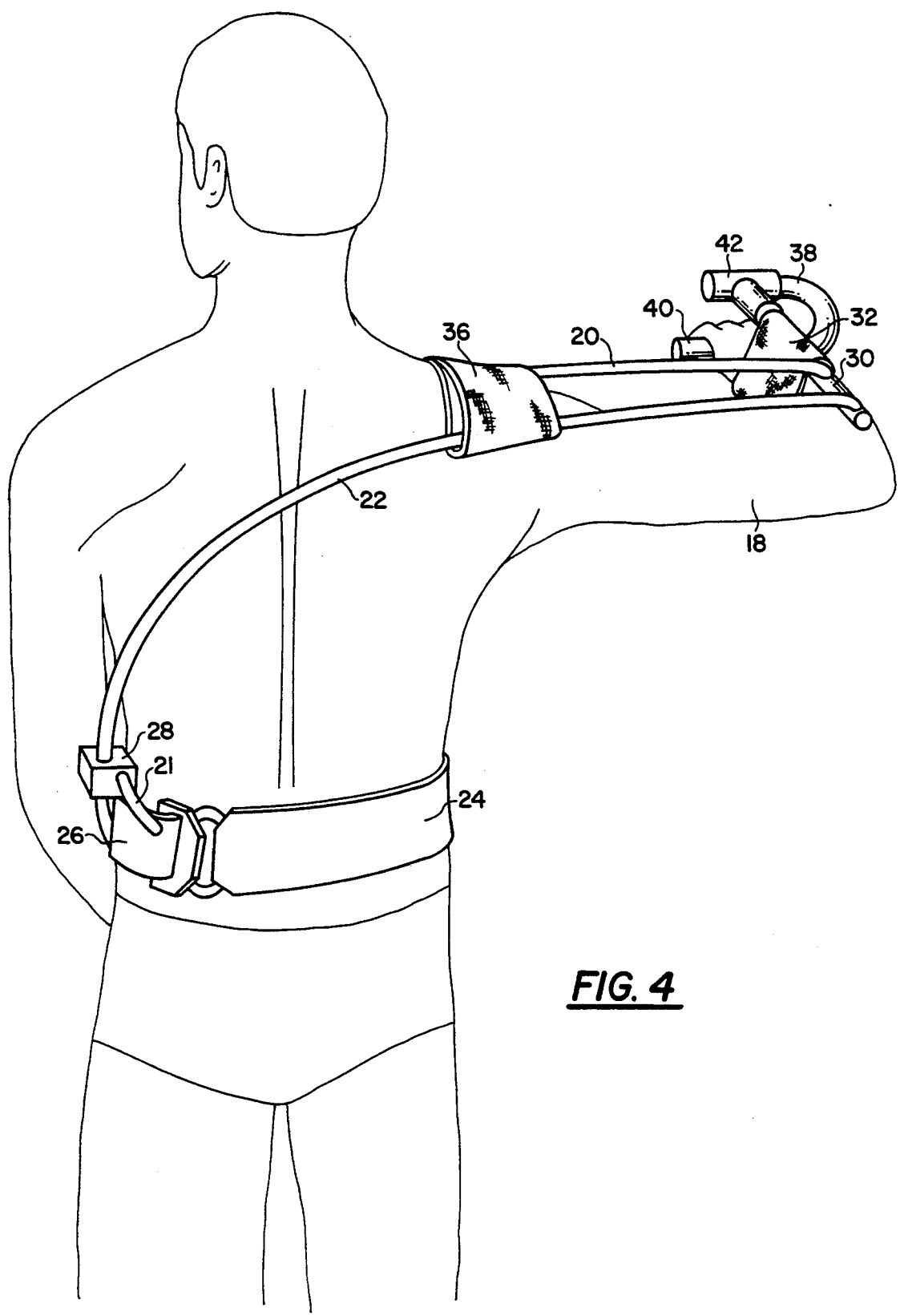
FIG. 4 is a rear perspective view of the invention shown in FIG. 2.
Figure 5:
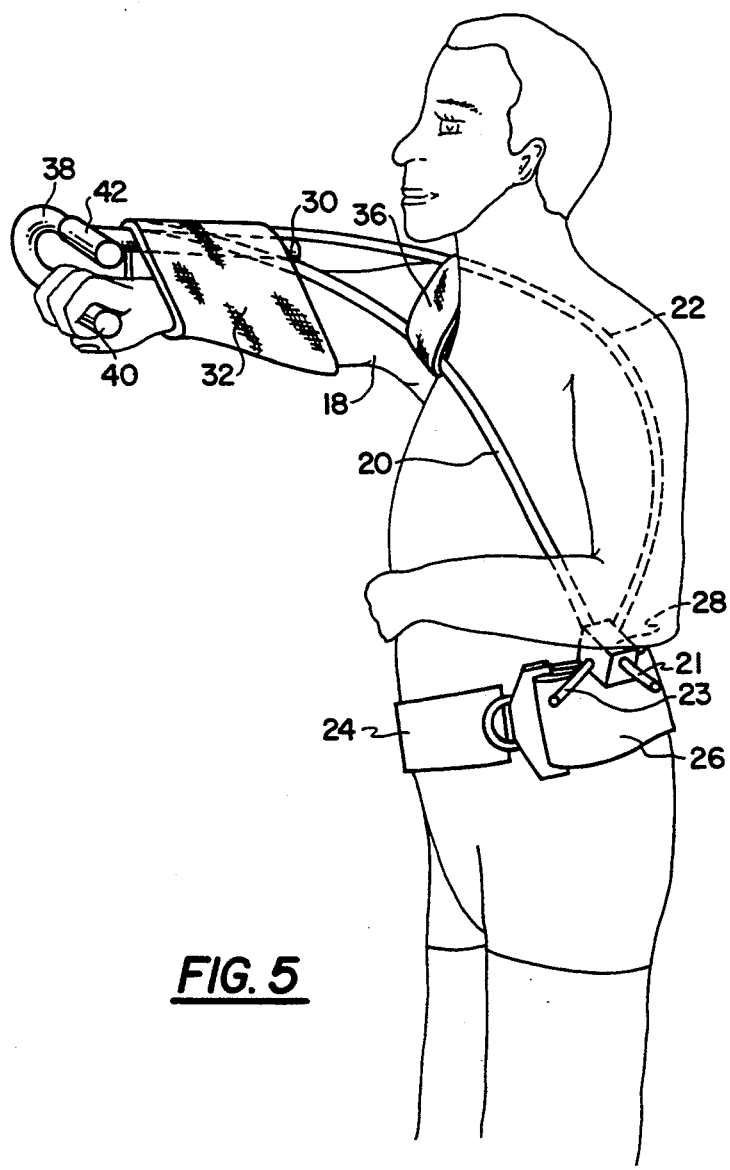
FIG. 5 is a side perspective view of the invention shown in FIG. 2.
Figure 6:
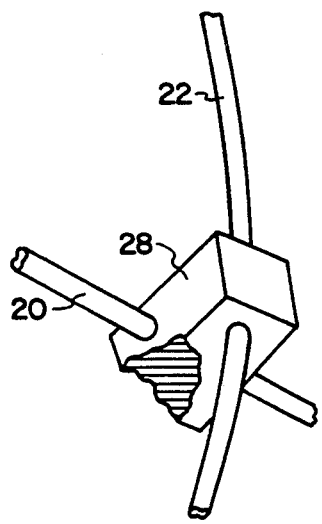
FIG. 6 is an enlarged perspective view, partially in section, of an adjustment device which is an element of the invention.

The support member 20 is attached to the rear end of strap 26. For example, as illustrated in FIGS. 3 and 4, member 20 extends from above the left buttock around the user's left side and then diagonally upwardly across the chest past the front of the right shoulder. Support member 22 is attached to the support strap 26 forwardly of member 20, and it extends around the left side of the user and then diagonally upwardly across the back past the rear of the right shoulder. The support members cross on one side of the user's torso where they pass through an adjustment device 28. Device 28 is a solid member, preferably made of metal or hard plastic, having separate passages drilled or formed therein to receive the respective support members in a snug but adjustable relationship. Thumb screws, or other conventional locking devices (not shown), are incorporated into the adjustment device 28 so that the support members may be retained in selected positions relative to device 28.

The support members 20 and 22 extend at their opposite ends beyond the wearer's shoulder and are connected to a support bar 30 which extends substantially perpendicular to the support members' axes at the points of connection. A tubular sleeve 32 is suspended from the support bar 30. The sleeve preferably is made of a fabric which provides comfortable support for a user's forearm 34. When the forearm 34 is placed through the sleeve 32 and rests thereon, the arm is suspended from the support bar, rather than being supported from underneath. Consequently, the underside of the upper arm, the armpit and side of the torso are accessible, rather than being covered with the complex and bulky underarm support structure which characterizes prior art shoulder braces.

The arm-supporting end of the shoulder brace is maintained in cantilevered relationship with the shoulder associated with the suspended arm, More particularly, as clearly shown in FIGS. 3 and 4, the support members 20 and 22 pass through a sleeve 36, preferably fabric, configured to rest on the right shoulder of the user.

An adjustable handgrip is associated with the forward end of the support bar 39. The handgrip comprises a U-shaped member 38 which is positioned in a plane normal to the longitudinal axis of support bar 30. The spaced legs of member 38 generally face in the direction of the user such that the lower leg 40 can be grasped by the hand associated with the supported arm. The upper leg 42 of member 38 is secured to a tubular element 44 which is dimensioned to function in telescoping operative relationship with support bar 30. By conventional adjustment means, the handgrip can be selectively positioned relative to bar 30 so as to comfortably accommodate the user's arm length.

The sleeve 32 and the handgrip arrangement just described permit the user to release the hand from leg 40 of member 38 and flex the elbow whereby the hand can move towards the user's face.

The shoulder brace just described is fully adjustable so that it can fit a wide variety of body shapes. This is accomplished by altering the effective length of the support members. To do so, the strap 24 is adjustable so as to be securable at different locations along the torso of the user. Also, the members 20 and 22 can be bent when they are formed of tubular metal, and movement of the support members 20 and 22 relative to the adjustment device 28 provides an additional means to change the effective lengths of the support members thereby permitting the desired orientation of the arm and shoulder to be achieved.

What is claimed is:

1. A shoulder brace adapted to be secured to a user's torso and configured to permit the suspension of an arm of the user therefrom, said brace comprising:
   first and second substantially rigid elongated support members;
   means for securing each of said members at one of its ends, to the user's torso at a location adjacent one side of the torso; said first and second members extending from said ends diagonally upwardly across respective front and back portions of the user's torso to locations at which opposite ends of said substantially rigid members are positioned above and laterally outwardly of the user's torso on the opposite side thereof; and
   means joined to said opposite ends of the support members for suspending the user's arm therefrom.

2. A shoulder brace according to claim 1, wherein said support members pass through a flexible sleeve located intermediate the ends of the respective members, said sleeve being adapted to rest on the shoulder of the user on said opposite side of the user's torso, whereby the arm suspending means is supported in cantilevered fashion by the torso.

3. A shoulder brace according to claim 1, wherein said support members are secured in spaced relationship at said one side of the user's torso and cross one another as they extend diagonally and upwardly from said ends, said brace further comprising:
   an adjustment device provided with passages to receive and selectively retain the respective support members at a location where they cross.

4. A shoulder brace according to claims 1, 2 or 3 wherein said suspending means comprises:
   a support bar connected to said opposite ends of the support members, said support bar extending substantially perpendicular to longitudinal axes of the support members; and
   an arm-receiving sleeve suspended from said support bar.

5. A shoulder brace according to claim 4, wherein said support bar is adjustable in length.

6. A shoulder brace according to claim 4, further comprising:
   a handgrip joined to a free end of said support bar.

7. A shoulder brace according to claim 6, wherein said support bar is adjustable in length.

8. A shoulder brace according to claim 6, wherein said handgrip comprises a substantially U-shaped member positioned in a plane substantially normal to a longitudinal axis of said support bar, said U-shaped member having an upper leg joined to said support bar and a lower leg adapted to be grasped by a hand associated with the user's suspended arm.

9. A shoulder brace according to claim 8, wherein said support bar is adjustable in length.

10. A shoulder brace according to claims 1, 2 or 3, wherein the said one ends of each of the support members are secured to an adjustable length belt surrounding the user's torso.

11. A shoulder brace according to claims 1, 2 or 3, wherein said support members are bendable.

12. A shoulder brace adapted to be secured to a user's torso and configured to permit the suspension of an arm of the torso therefrom, said brace comprising:

first and second substantially rigid elongated support members;

means for securing each of said members, at one of its ends, to the user's torso at a location adjacent one side of the torso, said first and second members extending from said ends diagonally upwardly across respective front and back portions of the user's torso to locations at which opposite ends of said substantially rigid members are positioned above and laterally outwardly of the user's torso on the opposite side thereof;

a flexible sleeve through which said members pass, said sleeve being located intermediate the ends of the respective members, said sleeve being adapted to rest on the shoulder of the user on said opposite side of the user's torso; and means joined to said opposite ends of the support members for suspending the user's arm therefrom.

13. A shoulder brace according to claim 12, wherein said suspending means comprises:

a support bar connected to said opposite ends of the support members, said support bar extending substantially perpendicular to longitudinal axes of the support members; and an arm-receiving sleeve suspended from said support bar.

14. A shoulder brace according to claims 12 or 13, wherein said support members are secured in spaced relationship at said one side of the user's torso and cross one another as they extend diagonally and upwardly from said ends, said brace further comprising:

an adjustment device provided with passages to receive and selectively retain the respective support members at a location where they cross.

15. A shoulder brace according to claim 13, wherein said support bar is adjustable in length.

16. A shoulder brace according to claim 14, wherein said support bar is adjustable in length.

17. A shoulder brace according to claim 13, further comprising:

a handgrip joined to a free end of said support bar.

18. A shoulder brace according to claim 17, wherein said support bar is adjustable in length.

19. A shoulder brace according to claim 17, wherein said handgrip comprises a substantially U-shaped member positioned in a plane substantially normal to a longitudinal axis of said support bar, said U-shaped member having an upper leg joined to said support bar and a lower leg adapted to be grasped by a hand associated with the user's suspended arm.

20. A shoulder brace according to claim 19, wherein said support bar is adjustable in length.

21. A shoulder brace according to claims 12 or 13, wherein the said ends of the support members are secured to an adjustable length belt surrounding the user's torso.

22. A shoulder brace according to claim 14, wherein the said ends of the support members are secured to an adjustable length belt surrounding the user's torso.

23. A shoulder brace according to claims 12 or 13, wherein said support members are bendable.

24. A shoulder brace according to claim 14, wherein said support members are bendable.

* * * * *